United States Patent [19]

Harrison

[11] 4,299,493
[45] Nov. 10, 1981

[54] AUTO-OPTICAL CENTERING DEVICE FOR PHOTOMETERS

[76] Inventor: Venton R. Harrison, 9407 Singleton Dr., Bethesda, Md. 20034

[21] Appl. No.: 101,667

[22] Filed: Dec. 10, 1979

[51] Int. Cl.³ ............................................. G01N 21/01
[52] U.S. Cl. .................................... 356/414; 356/244; 356/440
[58] Field of Search ............... 356/414, 416, 436, 440, 356/244; 250/573; 435/291

[56] References Cited

U.S. PATENT DOCUMENTS 3,441,352  4/1969  Hughes ............................ 356/39 X
3,489,525  1/1970  Natelson .
4,115,010  9/1978  McAleer ............................ 356/440

OTHER PUBLICATIONS

Journal of Clinical Microbiology; vol. 7, No. 1; Jan. 1978, pp. 55-58; "*Practical Colorimeter for Direct Measurement of Microplates in Enzyme Immunoassay Systems*"; Clem and Yolken.

Primary Examiner—Vincent P. McGraw
Attorney, Agent, or Firm—William G. Gapcynski; Werten F. W. Bellamy

[57] ABSTRACT

An automatic centering device for photometers which facilitates the automatic centering of each microtiter well is accomplished simply by moving the microtiter plate so that the stainless steel lamp housing tip is in proximity of the well. There is sufficient tension in the lamp support arm to automatically "nest", i.e. snugly fit the lamp source on the perimeter of the well being read and thus optically centering the light beam with the photodetector.

3 Claims, 1 Drawing Figure

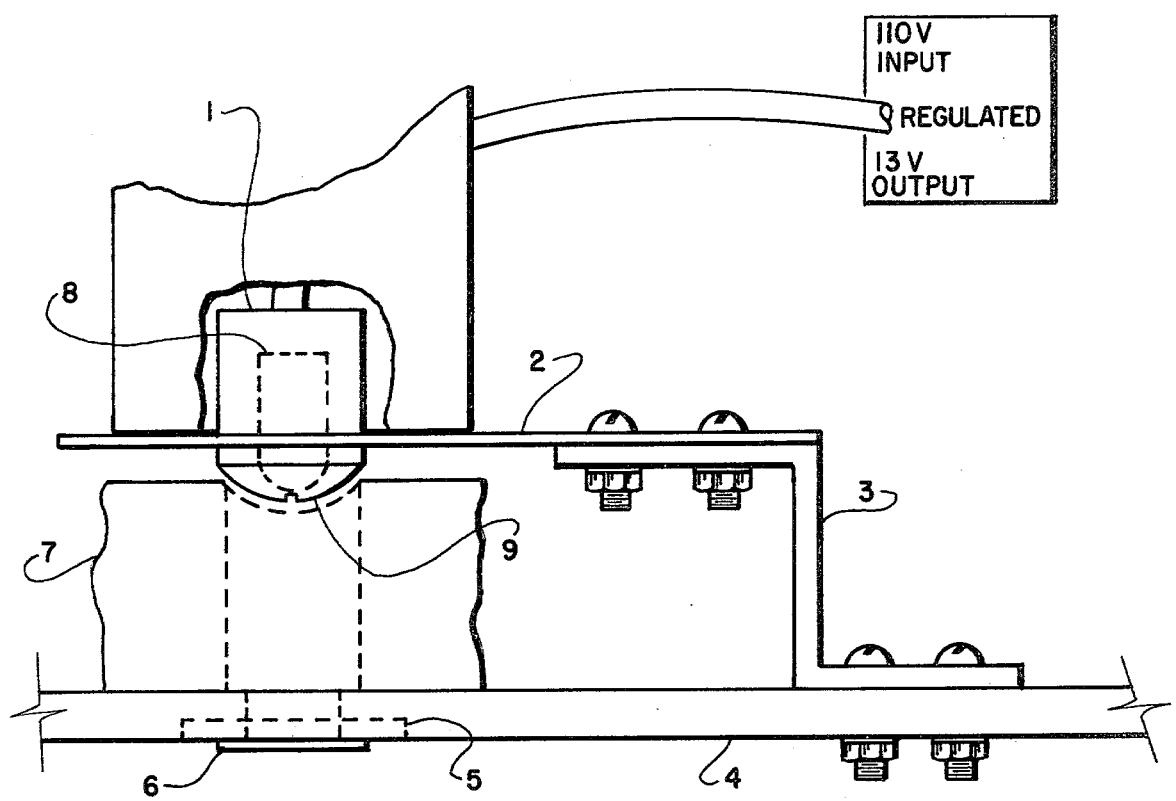

AUTO-OPTICAL CENTERING DEVICE FOR PHOTOMETERS

BACKGROUND OF THE INVENTION

This invention relates to an improved compact photometer primarily intended for use by individual scientists or physicians having limited laboratory space for conducting tests away from the laboratory (i.e. in the field).

The improved photometer of this invention is equipped with a novel automatic centering device.

The advent of such testing procedures as the Enzyme-Linked Immunosorbent Assay (ELISA) has come into widespread use in a growing number of laboratories engaged in the determination of immunologic parameters. This analytical ELISA test is performed by taking Colorimetric readings in microtiter plates. Although visual observation of the color changes (eyeballing) in the test is sometimes practiced, a much higher degree of accuracy can be achieved by reading the test in a microphotometer.

Recent attempts have been made to design colorimeters (photometers) which permit the direct measurement of microplates in enzyme immunoassay systems. Although some progress has been made in this area the devices designed to measure optical density in microtiter plates date have been very expensive. One problem in designing a colorimeter capable of making optical desity determinations in a microtiter plate is that each well must be identically aligned with the optical system. Otherwise there will be variation in the readings due to refractive differences.

The article by Thomas R. Clem et al, Journal of Clinical Microbiology, "Practical Colorimeter for Direct Measurement of Microplates in Enzyme Immunoassay Systems", Vol. 7, No. 1, January 1978, pages 55–58 describes a colorimeter in which the microtiter tray fits into a carrier that can be located at any of the 96 position wells of the microtiter tray in the path of the optical system.

U.S. Pat. No. 3,441,352 discloses a colorimeter having a plurality of photoelectric cells, each having associated with it a light filter which removes all except the particular monochromatic band of light to which the photoelectric cell is primarily responsive and where its peak response is located.

U.S. Pat. No. 3,489,525 discloses a colorimeter which measures out a test sample of the order of about 1 to 100 microliters, divides this sample into as many aliquots of test solution as desired and then analyzes each one individually and simultaneously using a revolving turntable mechanism for positioning the test samples.

SUMMARY OF THE INVENTION

The novel automatic centering device of the present invention for use on colorimeters aligns each reaction well of the microtiter plate with the optical detection system incorporated in a conventional microphotometer. The device requires no extraneous alignment mechanism and will function with microtiter plates produced by many different manufactures. The major problem facing all fabricators of microphotometers designed for use with microtiter plates is the alignment of each reaction well with the photometer detection system. This is due primarily to minute dimensional variations that occur during the plastic extrusion process employed in the production of the microtiter plate. Since there are 96 reaction wells in each microtiter plate, it is virtually impossible to have perfect alignment of 96 wells by any automated device. Thus scientists have been looking for ways to solve this problem. For the first time, by using the automatic centering device of the present invention, with the appropriate narrow band interference filters, can be used for an unlimited number of colorimetric tests performed in microtiter plates, such as ELISA, Lowry, Metabolic-inhibition and a host of blood chemistry determinations such as glucose, urea N, creatinine, etc., with appropriate filters. The automatic centering of the light beam in the path of the optical detector, allows the use of any brand of round or flat bottom microtiter plate and reading of test wells in any random sequence rapidly and reproducibly.

DESCRIPTION OF DRAWING

The FIGURE is a perspective view of the automatic centering instrument arrangement contemplated herein.

GENERAL DESCRIPTION

In the present invention, the automatic centering device consists of a flexible material such as plastic or stainless steel arm 2 supported at one end by an aluminum support bracket 3. The other end of the flexible arm 2 has mounted upon it an incandescent lamp 8 with plastic lamp housing 1. Over the incandescent lamp 8 is secured a ¼ inch diameter stainless steel tip 9 to allow light emission. The plastic lamp housing 1 is mounted and aligned directly above the optical filter (narrow band interference filter) 5 and silicon photocell (silicon photodetector) 6. The diameter of the stainless steel tip 9 is such that spring tension on the lamp housing 1 will depress the lamp 8 slightly below the perimeter of the reaction well of a microtiter plate 7, but not into it. Thus, if the reaction well is not initially placed precisely under the lamp 8 by the operator, the inherent spring tension of the support arm the lamp housing 1 will cause the stainless steel tip 9 to protrude slightly in the well and force the entire microtiter plate 7, consisting of 96 reaction wells, into proper position such that the readings of each well can be accomplished quickly, say about a two minutes, accurately, and with excellent reproducibility. There are microtiter plates produced by many manufacturing firms on the market today. Suprisingly, the novel device of the present invention seems to accommodate them all.

I claim:

1. An instrument for the analysis of a plurality of components of a single specimen equipped with an auto-optical centering device which comprises in combination:
   a. a flexible arm means for supporting the incandescent lamp at one end and mounted on an aluminum support bracket at the other end;
   b. an incandescent lamp enclosed in a plastic lamp housing which is mounted on the flexible arm;
   c. a stainless steel tip affixed in the lamp housing which contains an opening at its center to permit the emission of light therethrough;
   d. an optical filter and silicon photodetector located directly beneath the stainless steel tip; and
   e. a microtiter plate support tray to which is attached the aluminum support bracket which supports the flexible arm means.

2. The instrument of claim 1 wherein the flexible arm means is stainless steel.

3. The instrument of claim 1 wherein the flexible arm means is plastic.

* * * * *